United States Patent
Kuzma

[11] Patent Number: 6,119,044
[45] Date of Patent: Sep. 12, 2000

[54] COCHLEAR ELECTRODE ARRAY WITH POSITIONING STYLET

[75] Inventor: Janusz A. Kuzma, Englewood, Colo.

[73] Assignee: Advanced Bionics Corporation, Sylmar, Calif.

[21] Appl. No.: 09/259,199

[22] Filed: Mar. 1, 1999

Related U.S. Application Data

[63] Continuation-in-part of application No. 09/247,734, Feb. 9, 1999, which is a continuation-in-part of application No. 09/140,034, Aug. 26, 1998, Pat. No. 6,038,484.
[60] Provisional application No. 60/087,655, Jun. 2, 1997, and provisional application No. 60/079,676, Mar. 27, 1998.

[51] Int. Cl.$^7$ .................................................. A61N 1/05
[52] U.S. Cl. ............................................................ 607/137
[58] Field of Search ...................... 607/116, 137, 607/37, 122, 125; 600/595, 373, 377, 379

[56] References Cited

U.S. PATENT DOCUMENTS

| | | |
|---|---|---|
| 4,284,085 | 8/1981 | Hansen et al. . |
| 4,819,647 | 4/1989 | Byers et al. . |
| 4,832,051 | 5/1989 | Jarvik et al. . |
| 4,898,183 | 2/1990 | Kuzma . |
| 4,991,582 | 2/1991 | Byers et al. . |
| 5,000,194 | 3/1991 | van den Honert et al. . |
| 5,037,497 | 8/1991 | Stypulkowski . |
| 5,324,321 | 6/1994 | Pohndorf et al. . |
| 5,443,493 | 8/1995 | Byers et al. . |
| 5,545,219 | 8/1996 | Kuzma . |
| 5,578,084 | 11/1996 | Kuzma et al. . |
| 5,603,726 | 2/1997 | Schulman et al. . |
| 5,630,839 | 5/1997 | Corbett, III et al. ................... 607/137 |
| 5,645,585 | 7/1997 | Kuzma . |
| 5,649,970 | 7/1997 | Loeb et al. . |
| 5,653,742 | 8/1997 | Parker et al. . |
| 5,667,514 | 9/1997 | Heller . |
| 5,800,500 | 9/1998 | Spelman et al. ........................ 607/137 |

FOREIGN PATENT DOCUMENTS 9631087   3/1996   WIPO .

*Primary Examiner*—George R. Evanisko
*Attorney, Agent, or Firm*—Bryant R. Gold

[57] ABSTRACT

An implantable electrode array, adapted for insertion into either a left or right cochlea, assumes a spiral shape so as to hug the modiolar wall of the cochlea after insertion into the cochlea. All of the electrode contacts are spaced apart along one edge or side of the array, termed the "medial side", which medial side resides on the inside of the spiral. The electrode contacts are thus positioned in close proximity to the modiolar wall, closest to the ganglion cells that are to be stimulated by the electrode array. A positioning stylet made from a suitable memory wire is inserted into a longitudinal channel of the array. The stylet is made from memory wire and has properties selected to return to a desired memory spiral shape at or near body temperature (e.g., approximately 37° C. or 98.6° F.). The positioning stylet is cooled and bent as needed to assume a relatively straight, or non-spiral shape. While relatively straight, the stylet is slidably inserted into the longitudinal channel of the electrode array. The electrode array is then inserted into the cochlea in conventional manner. As the stylet within the electrode array warms to body temperature, it returns to its spiral memory shape, thereby causing the electrode array to also assume a spiral shape, thus positioning the electrode contacts of the electrode array against the modiolar wall.

14 Claims, 12 Drawing Sheets

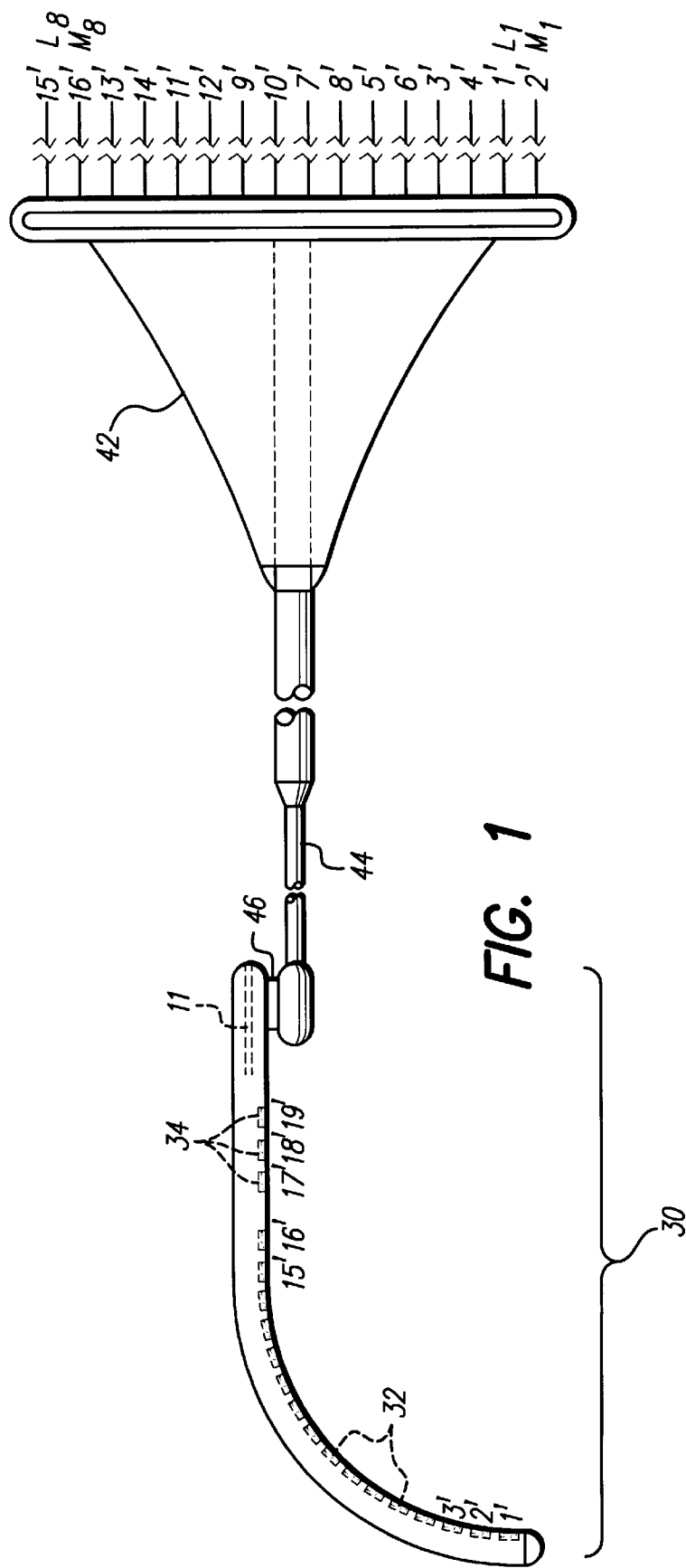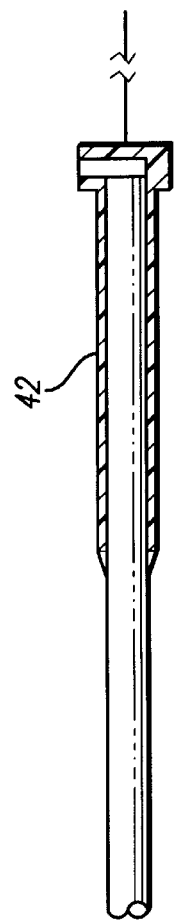

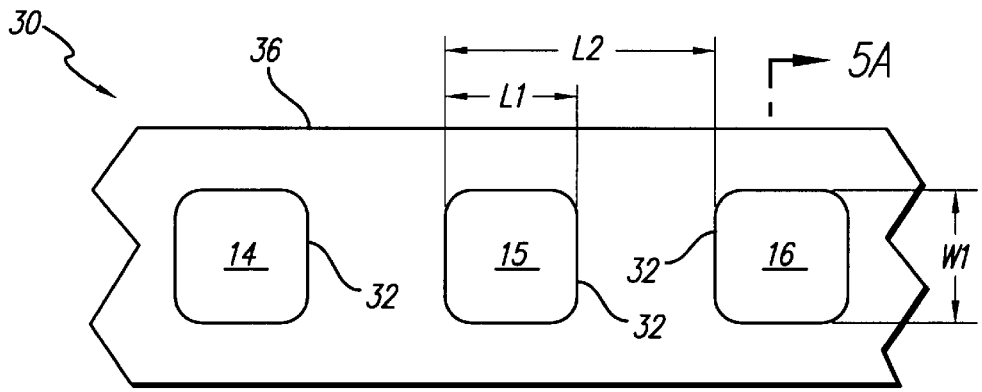
FIG. 5
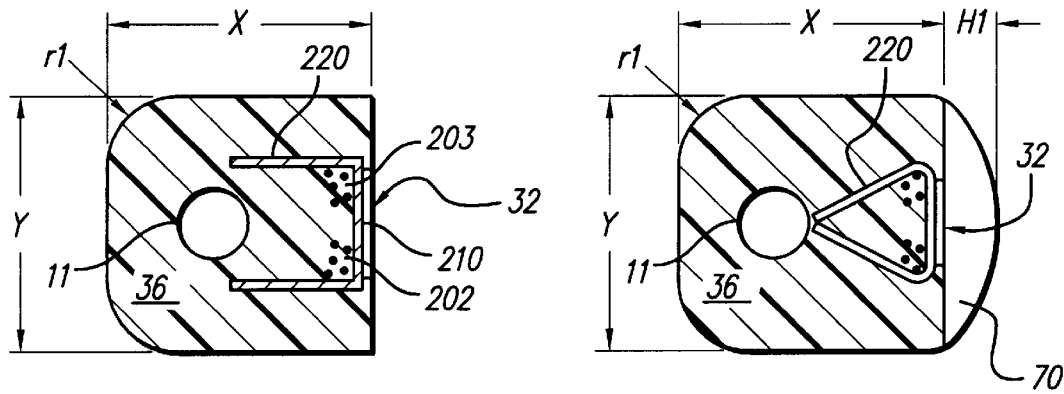
FIG. 5A
FIG. 6B
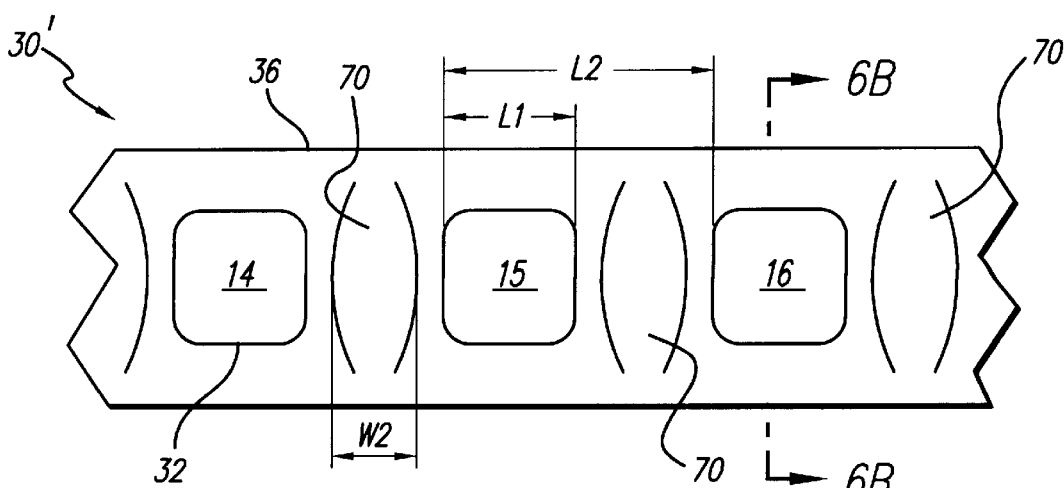
FIG. 6A

COCHLEAR ELECTRODE ARRAY WITH POSITIONING STYLET

This application is a continuation-in-part (CIP) of U.S. Application Ser. No. 09/247,734, filed Feb. 9, 1999, which is a CIP of U.S. Application Ser. No. 09/140,034, filed Aug. 26, 1998, now U.S. Pat. No. 6,038,484 and further claims the benefit of the following U.S. Provisional Patent Applications: Ser. Number 60/087,655, filed Jun. 2, 1997; and Ser. No. 60/079,676, filed Mar. 27, 1998; all of which patent applications are incorporated herein by reference.

BACKGROUND OF THE INVENTION

The present invention relates to implantable stimulation devices, e.g., cochlear prosthesis used to electrically stimulate the auditory nerve, and more particularly to an electrode array for insertion into the cochlea that hugs the modiolus of the cochlea, and further wherein the electrode contacts of the electrode array are on that side of the electrode array closest to the modiolus, thereby allowing the ganglion cells within the modiolus to be stimulated with minimal power consumption. That is, when the array is implanted into the cochlea, the electrode side of the array may be positioned closest to the modiolar wall, thereby placing all of the individual electrode contacts in close proximity to the ganglion cells and thereby in close proximity to the auditory nerve fibers.

Hearing loss, which may be due to many different causes, is generally of two types: conductive and sensorineural. Of these, conductive hearing loss occurs where the normal mechanical pathways for sound to reach the hair cells in the cochlea are impeded, for example, by damage to the ossicles. Conductive hearing loss may often be helped by use of conventional hearing aids, which amplify sound so that acoustic information does reach the cochlea and the hair cells. Some types of conductive hearing loss are also amenable to alleviation by surgical procedures.

In many people who are profoundly deaf, however, the reason for their deafness is sensorineural hearing loss. This type of hearing loss is due to the absence or the destruction of the hair cells in the cochlea which are needed to transduce acoustic signals into auditory nerve impulses. These people are unable to derive any benefit from conventional hearing aid systems, no matter how loud the acoustic stimulus is made, because their mechanisms for transducing sound energy into auditory nerve impulses have been damaged. Thus, in the absence of properly functioning hair cells, there is no way auditory nerve impulses can be generated directly from sounds.

To overcome sensorineural deafness, there have been developed numerous cochlear implant systems—or cochlear prosthesis—which seek to bypass the hair cells in the cochlea (the hair cells are located in the vicinity of the radially outer wall of the cochlea) by presenting electrical stimulation to the auditory nerve fibers directly, leading to the perception of sound in the brain and at least partial restoration of hearing function. The common denominator in most of these cochlear prosthesis systems has been the implantation into the cochlea of electrodes which are responsive to a suitable external source of electrical stimuli and which are intended to transmit those stimuli to the ganglion cells and thereby to the auditory nerve fibers.

A cochlear prosthesis operates by direct electrical stimulation of the auditory nerve cells, bypassing the defective cochlear hair cells that normally transduce acoustic energy into electrical activity in such nerve cells. In addition to stimulating the nerve cells, the electronic circuitry and the electrode array of the cochlear prosthesis performs the function of the separating the acoustic signal into a number of parallel channels of information, each representing the intensity of a narrow band of frequencies within the acoustic spectrum. Ideally, each channel of information would be conveyed selectively to the subset of auditory nerve cells that normally transmitted information about that frequency band to the brain. Those nerve cells are arranged in an orderly tonotopic sequence, from high frequencies at the basal end of the cochlear spiral to progressively lower frequencies towards the apex. In practice, this goal tends to be difficult to realize because of the anatomy of the cochlea.

Over the past several years, a consensus has generally emerged that the scala tympani, one of the three parallel ducts that, in parallel, make up the spiral-shaped cochlea, provides the best location for implantation of an electrode array used with a cochlear prosthesis. The electrode array to be implanted in this site typically consists of a thin, elongated, flexible carrier containing several longitudinally disposed and separately connected stimulating electrode contacts, perhaps 6–30 in number. Such electrode array is pushed into the scala tympani duct to a depth of about 20–30 mm via a surgical opening made in the round window at the basal end of the duct. During use, electrical current is passed into the fluids and tissues immediately surrounding the individual electrode contacts in order to create transient potential gradients that, if sufficiently strong, cause the nearby auditory nerve fibers to generate action potentials. The auditory nerve fibers arise from cell bodies located in the spiral ganglion, which lies in the bone, or modiolus, adjacent to the scala tympani on the inside wall of its spiral course. Because the density of electrical current flowing through volume conductors such as tissues and fluids tends to be highest near the electrode contact that is the source of such current, stimulation at one contact site tends to activate selectively those spiral ganglion cells and their auditory nerve fibers that are closest to that contact site. Thus, there is a need for the electrode contacts to be positioned as close to the ganglion cells as possible. This means, in practice, that the electrode array, after implant, should preferably hug the modiolar wall, and that the individual electrodes of the electrode array should be positioned on or near that surface of the electrode array which is closest to the modiolar wall.

In order to address the above need, it is known in the art to make an intracochlear electrode array that includes a spiral-shaped resilient carrier which generally has a natural spiral shape so that it better conforms to the shape of the scala tympani. See, e.g., U.S. Pat. No. 4,819,647. The '647 U.S. patent is incorporated herein by reference. Unfortunately, while the electrode array with spiral-shaped carrier shown in the '647 patent represents a significant advance in the art, there exists lack of sufficient shape memory associated with the carrier to allow it to return to its original curvature (once having been straightened for initial insertion) with sufficient hugging force to allow it to wrap snugly against the modiolus of the cochlea.

It is also known in the art, as shown in applicant's prior patents, U.S. Pat. Nos. 5,545,219 and 5,645,585, to construct an electrode carrier from two initially straight members, a rodlike electrode carrier and a flexible rodlike positioning member. As shown in these patents, the two members extend in substantially parallel relation to and closely alongside each other, but are connected to each other only at their respective leading and trailing end regions. After implant, a pushing force is applied to the positioning member so that it is forced to assume an outwardly arched configuration relative to the electrode carrier, thereby forcing the electrode carrier into a close hugging engagement with the modiolus, thereby placing the electrode contacts of the electrodes in as close a juxtaposition to the cells of the spiral ganglion as possible. The '219 and '585 U.S. patents are also incorporated herein by reference. The '219 patent, in particular, provides in FIGS. 1–10 and accompanying text an excellent summary of prior art electrodes and the deficiencies associated therewith.

Unfortunately, while the electrode array taught in the above-referenced '219 and '585 patents has the right idea, i.e., to force the electrode carrier into a close hugging engagement with the modiolus, it does so only by use of an additional element that makes manufacture of the lead more difficult and expensive, and only through application of an additional pushing force which is applied to an electrode structure after it is already fully inserted into the cochlea. Such additional pushing force may easily cause damage to the delicate scala tympani. Moreover, the entire electrode array may twist during the insertion process, or when the additional pushing force is applied, thereby causing the electrode contacts to twist and/or be forced away from the modiolus, rather than in a hugging relationship therewith.

Thus, while it has long been known that an enhanced performance of a cochlear implant can be achieved by proper placement of the electrode contacts close to the modiolar wall of the cochlea, two main problems have faced designers in attempting to achieve this goal. First, it is extremely difficult to assemble electrode contacts on the medial side of the an electrode array, facing the modiolus of the cochlea. Second, heretofore there has either been the need for application of an external (and perhaps unsafe) force, or a lack of sufficient shape memory, to allow the electrode (after initial straightening to facilitate insertion) to assume or return to the desired curvature needed to place the electrodes against the modiolar wall so that the curvature wraps snugly around the modiolus of the cochlea. As a result, the electrode contacts of the prior art electrodes are generally positioned too far way from the modiolar wall.

Many cochlear electrode arrays of the prior art are made for insertion into a left cochlea, or a right cochlea, depending upon the orientation of the electrode contacts one to another. It would be desirable for a universal electrode array to be made that could be used in either cochlea, left or right, without concern for whether the electrodes were orientated in a right or left side orientation.

It is thus evident that improvements are still needed in cochlear electrodes, particularly to facilitate assembling an electrode so that the electrode contacts are on the medial side of the electrode array, and to better assure that the electrode assumes a close hugging relationship with the modiolus once implantation of the electrode has occurred.

SUMMARY OF THE INVENTION

The present invention addresses the above and other needs by providing a universal electrode array, adapted for insertion into either a left or right cochlea, which assumes a spiral shape after insertion. Advantageously, all of the electrode contacts are spaced apart along one edge or side of the array, termed the "medial side", which medial side resides on the inside of the spiral. Hence, all of the electrode contacts are placed in close proximity to the modiolar wall, where they are closest to the ganglion cells that are to be stimulated.

The spiral shape of the universal electrode array is achieved through the use of a positioning stylet made from a suitable memory wire having properties selected to obtain the desired spiral shape at or near body temperature (e.g., approximately 37° C. or 98.6° F.). The positioning stylet is cooled to assume a relatively straight, or non-spiral shape. While still relatively straight, the stylet is slidably inserted into a lumen, or channel, that passes longitudinally through a carrier body of the electrode array. The electrode array is then inserted into the cochlea in conventional manner. As the stylet within the electrode array warms to body temperature, it assumes its spiral shape, thereby causing the electrode array to also assume a spiral shape, thus positioning the electrode contacts against the modiolar wall.

In an alternative embodiment, the positioning stylet is permanently inserted into the lumen of the carrier body of the electrode array. The entire array, including embedded stylet, is then cooled in order to straighten the array and allow it to be inserted into the cochlea. After insertion, the electrode array regains its spiral shape when heated to body temperature.

Advantageously, the structure of the electrode array facilitates bending of the array with the electrode contacts on the inside of the bend, yet deters flexing or twisting of the array that would tend to position or point the electrode contacts away from the inside of the bend. As a result, when the array is inserted into the scala tympani duct of a cochlea, and the spiral shape of the array is assumed by the memory shape of the positioning stylet, all of the electrode contacts on the medial side of the array end up facing the modiolus wall of the cochlea.

In the preferred embodiment, the electrode contacts of the array each comprise two strips of metal, arranged in a "T" shape (as viewed from a top view of the strips). During assembly, all of the "T" strips are held in a spaced apart, in-line, position on an iron sheet. Two wire bundles are formed that pass along each side of each "T". The leg of each "T" is folded over to pinch at least one of the wires from one of the wire bundles therebetween, which wire is then resistance welded to the strip. The sides of the "T" are then folded up and touch or nearly touch to form "Δ" or "U" shape (as viewed from a side view of the strips). The wire bundles going to other electrodes of the array pass through the "Δ" or "U". Silicone rubber, or a similar substance, is molded over and around the wire bundles and folded electrode T's, and a silicone tube, to form the carrier body of the electrode array. The silicone tube has a channel that passes therethrough having a diameter sized to allow the positioning stylet (wire with memory shape) to slide therein. The carrier body may be molded in a slightly curved shape in the region where the electrode contacts are located. The iron sheet is chemically etched away, leaving an array of spaced-apart electrode contacts along one edge of the flexible carrier, each having an exposed surface area that is typically flat with a rectangular shape. Each electrode contact area is electrically attached to at least one of the wires which passes through the carrier. A lumen or channel passes through the center of the carrier body.

Advantageously, the electrode array of the present invention can be manufactured using easy, low cost technology.

In one embodiment, small non-conductive bumps or humps are formed in the carrier between the electrode contact areas on the medial side of the array. These small bumps are made, e.g., from a soft silicone rubber, or equivalent substance. When inserted into the cochlea, the small bumps serve as non-irritating stand-offs, or spacers, that keep the electrode contacts near the modiolar wall, but prevent the electrode contacts from actually touching the modiolar wall. The bumps may also serve as dielectric insulators that help steer the stimulating electrical current in the desired direction, towards the modiolar wall, as taught, e.g., in copending U.S. patent application Ser. No. 09/137, 033, filed Aug. 28, 1998, assigned to the same assignee as the present application, and incorporated herein by reference.

Insertion of the electrode array into the cochlea may be performed in conventional manner, e.g., using the electrode insertion tool described in U.S. Pat. No. 5,443,493, incorporated herein by reference. Equivalent or similar insertion tools may also be used.

Advantageously, the electrode array of the present invention achieves the following goals: (1) it helps assure that the electrode contacts of the electrode array will be optimally positioned against the modiolar wall and facing the medial direction, e.g., facing the modiolar wall, in a cochlea of any size or any side (left or right) of the body; (2) it can be manufactured using easy, low cost technology; and (3) it can be easily inserted into the cochlea, and once inserted it assumes a desired, modiolus-hugging, spiral shape.

BRIEF DESCRIPTION OF THE DRAWINGS

The above and other features and advantages of the present invention will be more apparent from the following more particular description thereof, presented in conjunction with the following drawings wherein:

FIG. 1 depicts an electrode array and associated lead for attachment to an implantable cochlear stimulator in accordance with the present invention;

FIG. 2 illustrates a side view of the proximal end of the lead of FIG. 1;

FIG. 5 shows a detail view of the electrode array contacts of the electrode array of FIG. 4;

FIG. 5A is a sectional view of the electrode array taken along the line 5A—5A of FIG. 5;

FIG. 6A shows a detail view of the electrode array contacts of the alternative electrode array of FIG. 6;

FIG. 6B is a sectional view of the alternative electrode array taken along the line 6B—6B of FIG. 6A;

Corresponding reference characters indicate corresponding components throughout the several views of the drawings.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

Reference is initially made to Applicant's copending U.S. patent application, Ser. No. 09/216,063, filed Dec. 18, 1998, wherein there is described a flexible positioner for use with an implantable cochlear electrode array. This referenced '063 patent application is incorporated herein by reference. The flexible positioner described in the referenced '063 patent application is inserted into the cochlea, along with and behind an electrode array, thereby forcing the electrode array up against the modiolar wall. The electrode array of the present invention is designed for insertion into the cochlea without the need to use such a positioner. That is, as described more fully below, a positioning stylet is used with the electrode array of the present invention. This positioning stylet is made from a memory shape wire that assumes a spiral shape at or near body temperature, Thus, after the electrode array is inserted into the cochlea, and as the positioning stylet carried therein assumes its spiral shape, the electrode array also assumes a spiral shape. This spiral shape causes the electrode array to hug the modiolar wall, thereby positioning the electrode contacts of the electrode array against the modiolar wall, which is the desired goal. Thus, there should be no need to use a flexible positioner of the type described in the referenced '063 patent application with the electrode array of the present invention.

However, it should be pointed out that, if desired, there is nothing about the electrode array of the present invention that would prevent a flexible positioner of the type described in the '063 patent application from being used with it. Moreover, the techniques disclosed in the '063 patent application relative to the manner of making a flexible positioner are applicable to the present invention, particularly as they relate to the manner of overmolding a silicone tube to form a flexible body (whether that flexible body is used for a positioner or as the carrier of an electrode array) having a lumen or channel that passes longitudinally therethrough.

The advantageous features of the present invention will first be described with reference to FIGS. 12–16. Thereafter, other details of the electrode array will be presented in conjunction with FIGS. 1–11. It is noted that FIGS. 1–11 are generally the same as, and the description thereof generally follows, the description provided in Applicant's parent application, Serial Number 09/247,734, filed Feb. 9, 1999 (Attorney Docket No. AB-034A3), entitled "Cochlear Electrode Array With Electrode Contacts on Medial Side", previously incorporated herein by reference.

Figure 12:
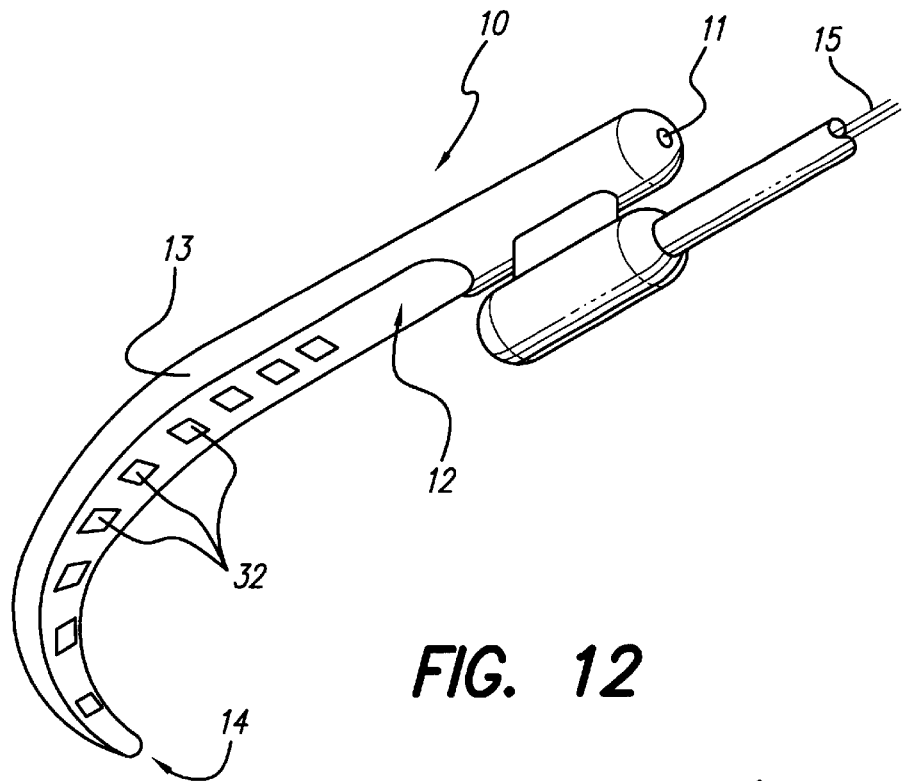
FIG. 12 is a perspective view of a universal electrode array formed on a flexible carrier made in accordance with the present invention.
Figure 14:
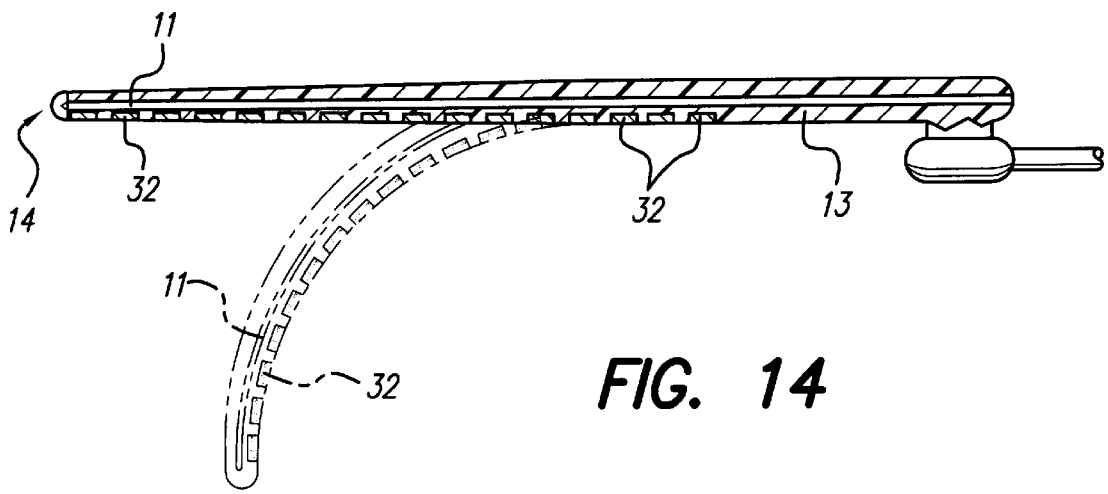
FIG. 14 is a side view of the electrode array of the present invention and illustrates a preferred shape of the electrode array absent the positioning stylet.

Turning first, then, to FIG. 12, there is shown a perspective view of a universal electrode array 10 made in accordance with the present invention. The array 10 includes a flexible carrier body 13 having a channel 11 that passes longitudinally therethrough. A multiplicity of spaced-apart electrode contacts 32 are formed on the carrier body, each of which is connected to a respective wire 15 that is embedded within the body 13. The flexible carrier body 13 may be molded from silicone rubber, or any other suitable flexible substance, as is known in the art. It may be molded to assume a relatively straight shape, as shown in FIG. 14, or a slightly curved shape, as shown by the phantom lines in FIG. 14.

The electrode contacts 32 are spaced apart along a medial side 12 of the carrier body 13. As explained below, the flexible carrier 12 is adapted to assume a spiral shape after insertion into the scala tympani of the cochlea. The medial side 12 is that side of the array 10 which is on the inside of the spiral, or inside of the curve of the spiral.

Figure 13:
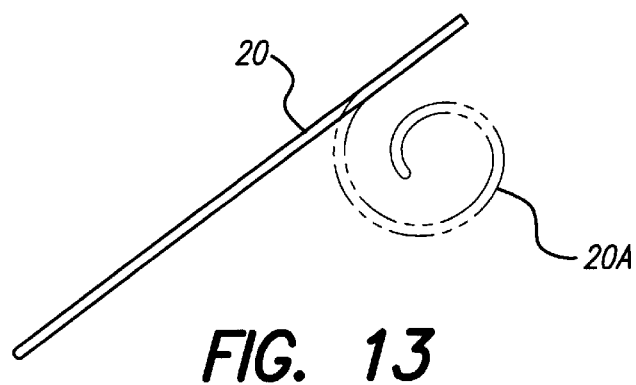
FIG. 13 shows a perspective view of a positioning stylet used with the invention, made from memory wire, and designed to assume a spiral shape, as shown by the phantom lines in FIG. 13, when raised to or near body temperature.

The channel 11 passes longitudinally through the flexible carrier body 13 up to a distal tip 14, where the channel is closed. The channel 11 has a diameter sufficiently large to allow a positioning stylet 20 to be slidably inserted therein from the proximal end. The positioning stylet 20 is shown in FIG. 13. It is made from a suitable memory wire, e.g., Nitinol Memory Wire, and has a diameter slightly less than the diameter of the channel 11. In a preferred embodiment, the stylet 20 has a diameter of about 0.1 mm. The properties of the wire from which the positioning stylet 20 is made are selected to obtain shape transformation at or near body temperature, e.g., at or a few degrees below 37° C. (or 98.6° F.). The memorized shape of the stylet 20 is in the form of a spiral 20A, as shown in the phantom lines of FIG. 13. This spiral shape preferably resembles or matches the average curvature of the cochlear modiolus.

Figure 15:
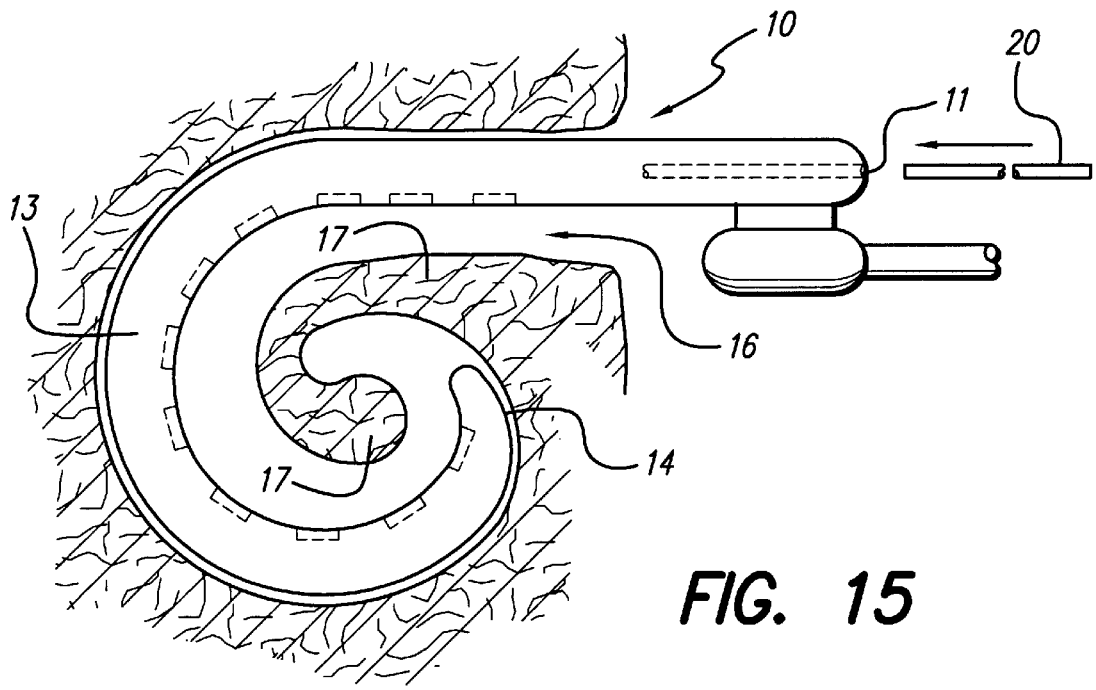
FIG. 15 is a schematic representation of a cross-sectional view of the scala tympani duct of the cochlea, illustrating the non-modiolus-hugging position of the electrode array of FIG. 14 when first inserted therein.

The electrode array 10 is inserted into the scala tympani duct 16 of the cochlea as illustrated in FIG. 15 using conventional electrode insertion techniques. Note that FIG. 15 is not intended to be anatomically accurate, but rather is just a schematic representation of a cross-sectional view of the spiralling scala tympani duct 16 of a cochlea. In the center of the spiraling tympani duct 16 is the modiolus 17, i.e., the conical central pillar of the cochlea. It is within the modiolus where the ganglion cells are located that are stimulated by electrical currents flowing from or to the electrode contacts 32 of the array 10.

The position of the electrode array 10 shown in FIG. 15 represents the non-modiolus-hugging position of the electrode array 10 when first inserted into the cochlea. As seen in FIG. 15, the array 10 resides against the outer wall of the duct 16 with the electrode contacts 32 being positioned some distance from the modiolus 17.

In accordance with the present invention, the positioning stylet 20 is straightened at a low temperature, i.e., at a temperature below the shape transformation temperature. The straightened stylet 20 is gradually inserted into the channel 11 of the electrode array 10 until the tip of the stylet wire reaches the distal tip 14 of the array.

Figure 16:
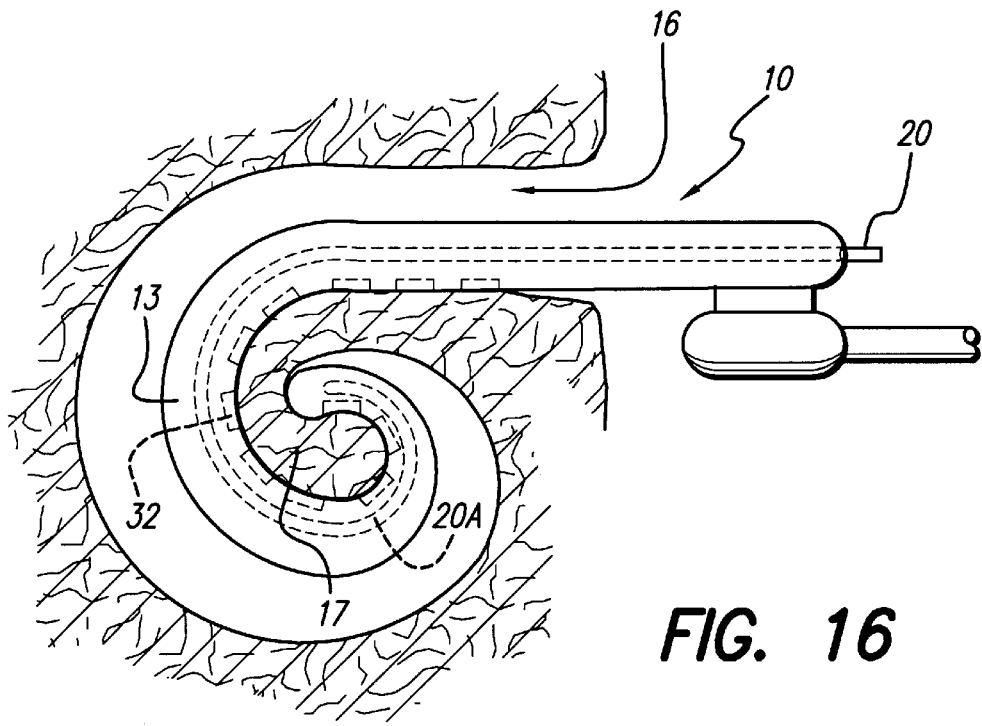
FIG. 16 is a schematic representation as in FIG. 15, showing the modiolus-hugging position of the electrode array after insertion of the positioning stylet therein, and after the positioning stylet has assumed its memory spiral shape.

During insertion and after, the positioning stylet 20 warms to body temperature and recovers its curved shape 20A. In the process, the positioning stylet 20 relocates the electrode array 10 to the preferred modiolus-hugging position shown in FIG. 16. As seen in FIG. 16, the electrode contacts 32 are in close proximity to the modiolus 17, and hence in close proximity to the spiral ganglion cells that are to be stimulated.

In an alternative embodiment, the memory-shaped stylet wire 20 is permanently inserted into the channel 11 of the electrode array body 13. Before insertion, the stylet wire and electrode array 10 are straightened at a low temperature. Once inserted into the cochlea, the array 10 assumes its spiral shape as the stylet 20 recovers its memory spiral shape.

It should be noted that in order for the array 10 to be able to be straightened and thereafter curved or spiraled, it is necessary that the stylet 20 be free to slide within the channel 11. Otherwise, binding would occur, and the stylet wire 20 would be prevented from recovering its curved shape.

Next, additional details associated with a particular embodiment of the electrode array 10 will be described. These details teach one type of implantable electrode array having multiple, in-line, electrode contacts that may be used with the invention. Here, the term "in-line", used to describe the electrode contacts, means only that the electrode contacts are spaced apart more or less in alignment with the longitudinal axis of a lead. It does not mean that a perfect, straight alignment with the lead axis must be achieved. For example, electrode contacts that zigzag somewhat with respect to the lead axis would still be considered to be in-line electrodes for purposes of the present invention. Thus, in general, "in-line" means that of two adjacent electrode contacts, one will be more distal than the other. Further, all of the in-line electrode contacts will have an exposed surface which, more or less, lies on the same side—the medial side—of the curved electrode.

The electrode array 10 of the present invention may be best used with an implantable multichannel pulse generator, e.g., an implantable cochlear stimulator (ICS) of the type disclosed in U.S. Pat. No. 5,603,726, incorporated herein by reference, or other suitable stimulator. It is to be understood, however, that although a cochlear electrode array is hereafter described, having dimensions suitable for insertion into the cochlea, the principles of the invention may be applied to other types of implantable leads for applications other than cochlear stimulation.

The electrode array of the present invention is particularly adapted to bend or flex in one direction, thereby making it suitable for insertion into a curved body cavity, such as the cochlea, and thereafter assuming a curved or spiral shape as guided by the memory shape of the stylet wire 20.

An important feature of the electrode array of the present invention is that all of the active electrode contacts of the array are generally positioned along one side, e.g., the medial side (the inside of the curve or bend), of the array. Thus, when inserted into the curved or spiraling cochlea, which may advantageously be either a left or right cochlea, wherein the cells to be stimulated are located within the center modiolar wall, the electrode contacts are positioned proximate the modiolar wall, where they are closest to the cells to be stimulated. Hence, the electrode array of the present invention facilitates stimulation of the desired cells at lower power levels than would otherwise be needed if the electrode contacts were not proximate the modiolar wall.

Another feature of the electrode array of the present invention is that the electrode contacts have, in the preferred embodiment, a relatively large exposed electrode surface area that is generally planar or flat having a desired geometric shape, e.g., rectangular, semicircular, or oval. However, it is to be understood that the principles of the invention may also be practiced with electrodes that have exposed surface areas that are not flat, e.g., dimpled, or corrugated, or pitted, and that may have an exposed surface area that has irregular geometric shapes.

Except as noted herein, the materials from which the electrode array of the invention is made, and the manner of making the electrode array, may be conventional, as are known in the art.

A preferred electrode array 30 in accordance with the present invention is shown in FIG. 1. (Note, while the reference numeral 30 is used to identify the electrode array of FIGS. 1–11, it is to be understood that this electrode array 30 is the same as the electrode array 10 shown in FIGS. 12–16.) The electrode array 30 forms the distal end of a lead/array assembly 40 adapted to be connected to an implantable cochlear stimulator (ICS), not shown. The lead/array assembly 40 includes the electrode array 30, a fantail proximal connector 42, and a lead body 44 connecting the array 30 to the proximal connector 42. The ICS is typically housed within a ceramic or other case, such as is disclosed in U.S. Pat. No. 4,991,152, incorporated herein by reference. The case has an array of feedthrough terminals corresponding to its multiple channels. A preferred ICS has eight channels, with each channel having two feedthrough terminals connected thereto. Such terminals are typically labeled as M1 and L1 (for medial and lateral) for the first channel, M2 and L2 for the second channel, and so on, up to and including M8 and L8 for the eighth channel.

The feedthrough terminals are spaced across a header of the case. Inside the case, each feedthrough terminal is connected to appropriate electronic circuitry for the corresponding channel, as taught in the previously-referenced '726 patent. On the outside of the case, each feedthrough terminal is connected to a corresponding wire conductor within the lead/array assembly 40. Such wire conductors are identified in FIG. 1 by the numbers 1' through 16'. The wire conductors 1'–16' are of necessity spread out at the point where they connect to the feedthrough terminals of the header. Thus, the proximal end of the lead/assembly 40 includes the fantail connector 42 that funnels the spread conductors 1'–16' at the point they connect to the feedthrough terminals down to the lead body 44. A side view of the fantail connector 42 is shown in FIG. 2.

The manner of forming the fantail connector 42, and connecting it to the feedthrough terminals may be conventual, and does not form part of the present invention. Rather, the present invention is directed to the electrode array 30 at the distal end of the lead/assembly 40. It should be emphasized that the electrode array 30 is not limited to use with a proximal fantail connector 42 and the type of ICS disclosed in the '726 patent. Rather, the electrode array 30 may be used with any type of proximal connector that interfaces with an appropriate pulse generator.

As seen in FIG. 1, the electrode array 30 may be curved an appropriate amount. A multiplicity of in-line electrode contacts 32 are spaced apart so as to lie on the medial side (inside of the curve) of the array. Sixteen such electrode contacts 32 are used in a preferred embodiment of the array 30. These electrode contacts are respectively connected to the wire conductors 1'–16' within the lead. As shown in FIG. 1, the most distal electrode contact, for example, may be connected to wire conductor 1' within the lead 44, which in turn is connected to the feedthrough terminal L1 at the pulse generator. The second-most distal electrode contact may similarly be connected to wire conductor 2' within the lead 44, and may be connected to the feedthrough terminal M1 at the pulse generator. In this manner, the two-most distal electrode connectors 32 on the array may be connected to the first channel of the implantable pulse generator. In a similar manner, the two most proximal electrode contacts on the array 30 may be connected to wire conductors 15' and 16' within the lead 44, and may be connected, e.g., to feedthrough terminals L8 and M8, corresponding to the eighth channel, of the implantable pulse generator. The other electrode contacts 32 included within the array 30 may be similarly connected to a corresponding channel within the pulse generator.

As further seen in FIG. 1, the preferred electrode array 30 also includes three reference electrode contacts 34, identified in FIG. 1 by the electrode numbers 17', 18' and 19'. Such reference contacts 34 are not connected to any wire conductors within the lead 44, and for this reason are sometimes referred to as "dummy reference contacts". Rather, each of these reference contacts 34 may provide a reference indicator or marker to the physician inserting the electrode array relative to the depth of insertion.

As also seen in FIG. 1, the lead/array assembly 40 further includes an offset portion 46 that effectively marks the end of the lead 44 and the beginning of the electrode array 30. Such offset portion 46 facilitates insertion of the electrode array 30 into the scala tympani duct of the cochlea. The insertion process may be conventional, and is aided by a special tool of the type disclosed in the '493 patent, previously referenced.

Figure 3:
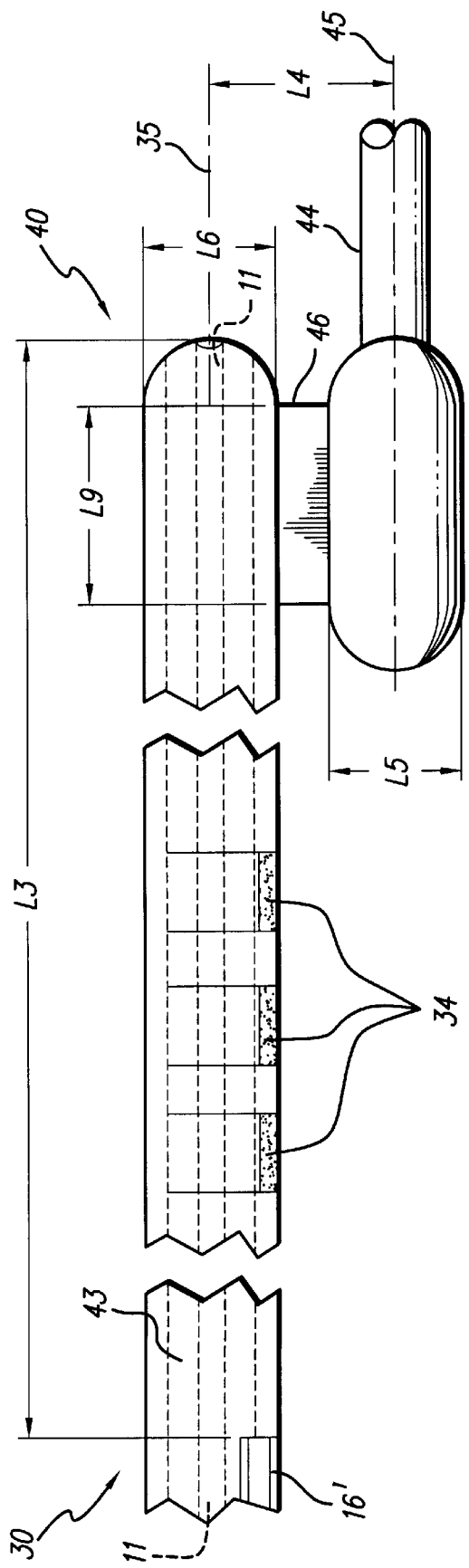
FIG. 3 is a more detailed view of the offset portion of the lead/array of FIG. 1.

Turning next to FIG. 3, there is shown a more detailed view of the offset portion 46 of the lead/array 40. As seen in this figure, the offset portion 46 separates the body of the lead 44 from the body of the array 30 by an offset distance L4. When measured from a center-line longitudinal axis 45 of the lead 44 to a center-line longitudinal axis 35 of the array 30, this distance L4, in the preferred embodiment, is about 1.3 mm. At the point of the offset, the diameter of the lead 44 is a distance L5, while the diameter of the electrode array is a distance L6. In the preferred embodiment, both L5 and L6 are about 0.8 mm. The length L9 of the offset portion 46 is approximately 1.6 mm, allowing the wire conductors 1'–16' within the electrode array 30 to transition to the lead body 44 without too sharp of a bend. It is to be understood that these dimensions, as well as other dimensions presented herein, are only exemplary of one embodiment, and are not meant to be limiting.

Typically, as seen in FIG. 3, the electrode array is molded over a silicone rubber tube 43, which tube 43 provides the channel 11 through which the positioning stylet 20 is inserted. The outer diameter of the tube 43 may be, e.g., approximately 0.64 mm.

The material from which the lead/array 40, including the electrode array 30, is made may be any suitable biocompatible material commonly used with implantable leads and other implantable components as is known in the art. A suitable material, for example, is a type of silicone polymer or rubber known as LSR-70 or LSR-25. The properties of LSR-70 and LSR-25 are well known in the art, and LSR-70 and LSR-25 may be obtained commercially from numerous sources,. LSR-70 is formed into a desired shape by injecting or otherwise inserting it into a mold while in a liquid state and allowing it to cure in the mold at a specified temperature for a specified time period. For example, LSR-70 may cure at a temperature of 140 degrees C. for about 15 minutes. LSR-25 may likewise be formed into a desired shape using a similar molding process, or it may be applied through a suitable applicator, e.g., a syringe, to a desired area and then formed into a desired shape. LSR-25 is essentially the same as LSR-70 except that when it cures it is significantly softer, i.e., more pliable. Both LSR-70 and LSR-25 readily adhere to the tubing 43 so that when cured they become integral therewith.

Still with reference to FIG. 3, it is seen that the distance from the proximal end of the electrode array 30 to the proximal edge of electrode contact 16' (i.e., the electrode contact 32 that is connected to wire conductor 16') is a distance L3. In one particular embodiment, the distance L3 is about 10.5 mm.

Figure 4:
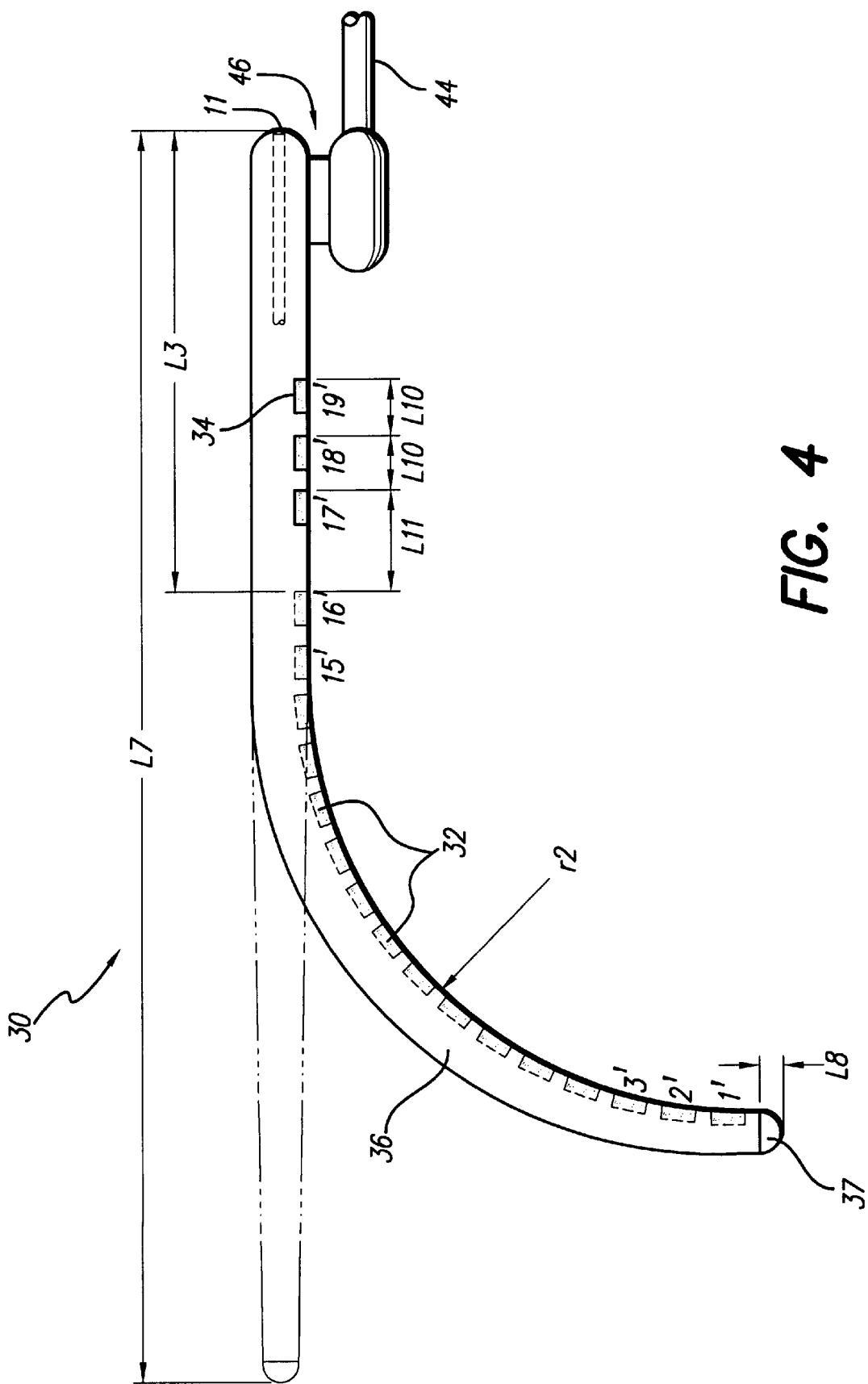
FIG. 4 shows the electrode array of the present invention having spaced-apart electrode array contacts along the medial side of the array, which electrode array comprises the distal end of the lead/array of FIG. 1.

Next, with reference to FIG. 4, a more detailed view of the electrode array 30 is shown. The electrode array includes electrode array contacts 32 equally-spaced along a medial side of a flexible carrier 36. The flexible carrier 36 is made from LSR-70, and is molded around an assembly of electrode contacts 32 and interconnecting wires as described below in conjunction with FIGS. 7A–11. The electrode array 30 has an overall length L7. Such length L7 is most easily measured when the array 30 is straightened, as shown by the phantom lines in FIG. 3. In the preferred embodiment, L7 has a value of approximately 25 mm. While the electrode array 30 could be formed to assume any desired shape, in the preferred embodiment it is formed to include a natural curve having a radius of curvature r2, with the electrode contacts 32 being positioned along the inside of the curve. The radius of curative r2 may have a value of approximately 9.0 mm.

As further seen in FIG. 4, a soft tip 37, having a depth of distance L8, is typically formed from LSR-25 at the very distal tip of the electrode array 30. In the preferred embodiment, L8 has a value of approximately 0.3 mm.

As additionally illustrated in FIG. 4, the reference marker contacts 34, identified as electrodes 17', 18' and 19', are spaced from the active electrode 16' a distance L11, with a spacing between the reference marker electrodes of L10. In the preferred embodiment, the distance L11 is about 3.0 mm, and the distance L10 is about 1.0 mm.

Referring next to FIG. 5, the preferred spacing between the individual electrode contacts 32 is depicted. Such spacing, as well as all the other dimensional detail presented herein, is exemplary of a cochlear electrode, and is not intended to be limiting. As seen in FIG. 5, each exposed electrode contact surface area comprises a generally rectangular-shaped area having a length L1 and a width W1. Other shapes could also be used. In one embodiment, the rectangular area is roughly a square, with L1 and W1 each having a value of approximately 0.4 mm ±10%, thereby providing an exposed electrode surface area of approximately 0.16 mm$^2$. The spacing between corresponding points of adjacent electrode contact areas 32 is a distance L2. L2 has a nominal value of approximately 0.9 mm±0.1 mm.

The electrode contact areas comprise an exposed surface of an electrode contact 32 that is formed from folded strips 210 and 220 of a biocompatible metal, such as platinum, as described more fully below in conjunction with FIGS. 7A–8D. Such electrode contacts are embedded within the molded carrier 36 as illustrated in the sectional view of FIG. 5A, which is taken along the lines 5A–5A of FIG. 5. As seen in FIG. 5A, the carrier 36 is formed to have a cross-sectional area that is generally rectangular, having dimensions of X by Y mm, where the values of X and Y vary as a function of where along the length of the carrier the cross section is viewed. At electrode 16 (near the proximal end of the electrode/array 30), for example, X and Y are both about 0.8 mm. At electrode 1 (near the distal tip of the electrode array), X and Y are both about 0.6 mm. Thus, it is seen that the carrier 36 is tapered along its length so that it has a smaller cross section at its distal tip than it does at its proximal end.

Still with reference to the cross-sectional view of the array shown in FIG. 5A, it is seen that the sectional shape has rounded corners on the side opposite the medial side. (As explained previously, the medial side is the side where the electrode contacts 32 are located.) The rounded corners have a radius of curvature r1 that is approximately 0.3 mm in one representative embodiment.

The electrode contacts 32 have a general cross sectional shape, as seen in FIG. 5A, and as will be more evident from the description below of FIGS. 7A–8D below, that resembles a triangle or a "U". The base of this triangular-shaped (or "Δ-shaped") or U-shaped electrode forms the exposed electrode contact area along the medial side of the electrode array, e.g., as seen in FIG. 5. The upward sloping legs 220 of this Δ-shaped or U-shaped electrode extend into the body of the carrier, e.g., as anchors, and thus become embedded (non-exposed) portions of the electrodes. That is, the legs 220 extend into the body of the carrier, in some fashion, so that the electrode is firmly anchored in its desired position along the length of the array. The lumen 11 passes through the central portion of the body of the carrier. In some embodiments, the legs 220 may be completely folded over so as to lie almost flat on top of the exposed surface area, as shown generally in parent application (Ser. No. 09/140,034 now U.S. Pat. No. 6,038,484). In other embodiments, the legs 220 may extend more or less straight into the body of the carrier, forming a generally block "U" cross-sectional shape, as shown in FIG. 5A. In other embodiments, the legs 220 may slope so as to generally form a triangle, or Δ-shape, as illustrated, e.g., in FIG. 6B.

Wire bundles 202 and 203 pass through the corners of the Δ-shaped, U-shaped (or other-shaped) electrodes and become embedded within the molded carrier 36 when formed. As explained in more detail below, at least one wire from at least one of these wire bundles makes electrical contact with each active electrode. The wires that do not make electrical contact with an electrode contact are nonetheless engaged by or supported by the embedded portion of the electrode as they pass through the Δ or U (or other) shape. Such engagement helps support and position the wire bundles prior to molding the carrier over them. Moreover, the location of the wire bundles immediately behind and along opposing edges of the exposed surface area of the electrodes helps add additional stiffness to the electrode array, once formed, in the lateral direction, as explained below, thereby making it more difficult to bend or twist the array in the lateral direction. In contrast, the array remains relatively easy to bend in the medial direction. As used herein, the medial direction is the direction of curvature defined by the radius r2 (FIGS. 4 and 6).

Figure 6:
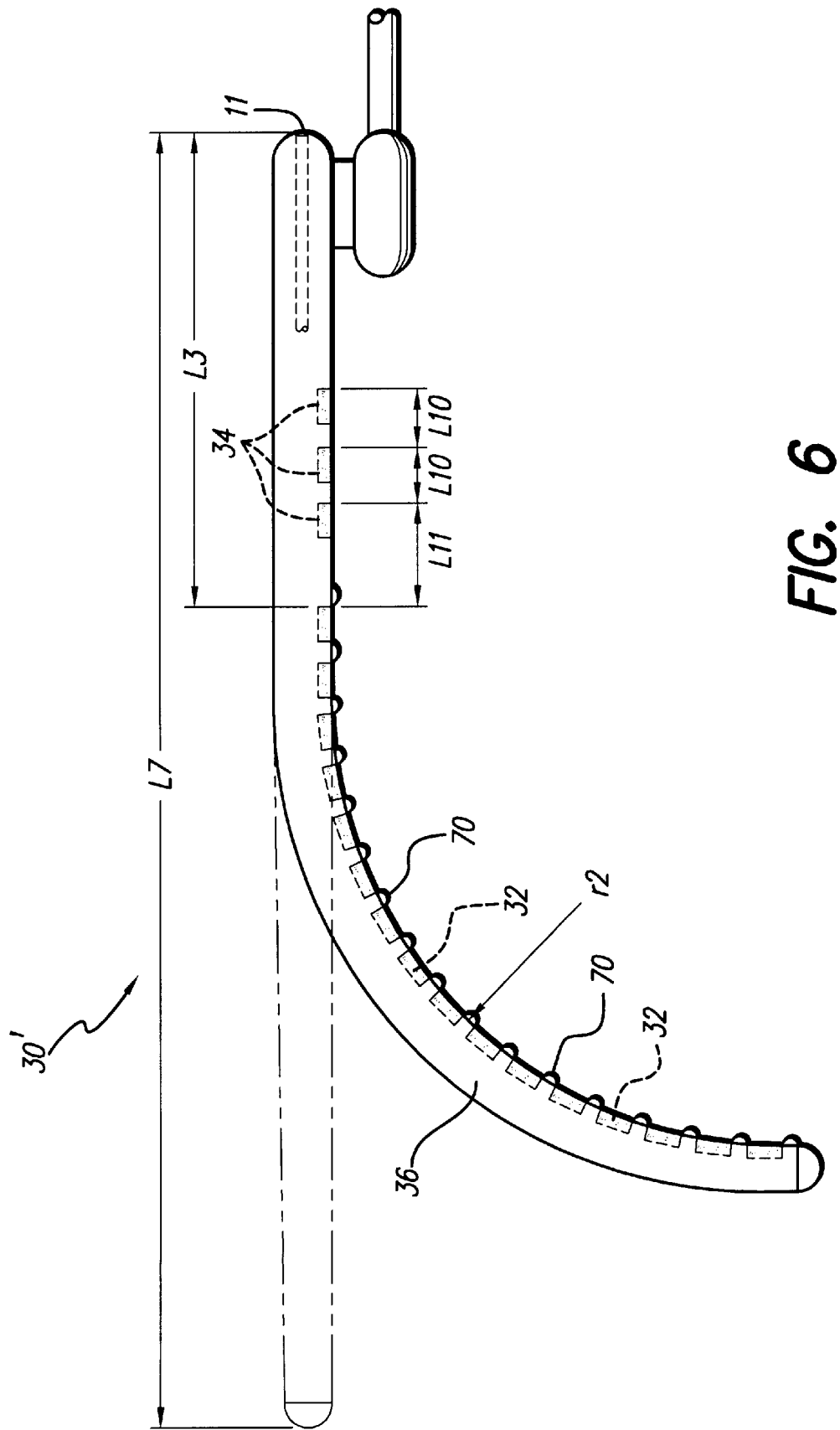
FIG. 6 shows an alternative embodiment of the electrode array of the present invention wherein bumps are formed in the space between each electrode contact.

An alternative embodiment an electrode array 30' made in accordance with the present invention is shown in FIGS. 6, 6A and 6B. This alternative electrode array 30' is the same as the array 30 illustrated in FIGS. 4, 5 and 5A with the exception that a series of small non-conductive bumps, or humps 70, are formed between the electrode contact areas 32. As seen best in FIG. 6B, these humps 70 have a height H1 of about 0.13 mm, and as seen best in FIG. 6A, have a width W2 of about 0.25 mm. As further seen best in FIG. 6, the humps 70 extend out from the medial surface of the electrode array. The humps 70 are made from a soft silicone rubber, or equivalent substance, such as LSR-25. When inserted into the cochlea, the small bumps 70 serve as non-irritating stand-offs, or spacers, that allow the electrode contacts 32 to be positioned near the modiolus wall, but prevent the electrode contacts 32 from actually touching the modiolus wall. The humps 70 further serve as dielectric insulators that help steer the stimulating electrical current, flowing to or from the electrode contacts, in the desired direction, from or towards the cells located in the modiolus wall, as taught, e.g., in the previously referenced copending U.S. patent application Ser. No. 09/137,033. Except for the presence of the humps 70, FIGS. 6, 6A and 6B correspond to FIGS. 4, 5 and 5A.

One of the advantages of the present invention is that the electrode array is easy and relatively inexpensive to manufacture. A preferred method of making the electrode array 30 or 30' is illustrated, for example, in FIGS. 7A through 11. It is to be emphasized that the method depicted in these figures of making the electrode array is not the only way an electrode array 30 or 30' could be made. However, it represents an easy and inexpensive (and thus a preferred) way to make the electrode array.

Most designs of electrodes and connectors are based on the principle of molding a contact or array of contacts, usually made from biocompatible metal, into a polymer carrier like silicone or polyurethane rubber. The electrode contacts are usually required to be located in a controlled position in reference to the surface of the carrier, with specified surface areas to be fully exposed to the stimulated or interconnection area. Disadvantageously, making such electrodes or connectors becomes extremely difficult, especially when the contacts are very small and/or a large number of contacts are required, e.g., as is the case with a cochlea electrode. One of the main problems encountered in the fabrication of such electrodes or connectors is to find a reliable method of holding the system of contacts in the desired and stable position during the process of welding the connecting wires and molding the polymer carrier. A further problem relates to maintaining a controlled surface of the contacts that are to remain exposed, i.e., to ensure that the contacts are not covered by the polymer when the carrier is molded.

The preferred methods of making the electrode array 30 or 30' described below in connection with FIGS. 7A through FIG. 11 are based on the principle of attaching (by the process of resistance welding) electrode contacts made from precious, biocompatible material (such as platinum or its alloys) to a foil carrier made from a non-toxic but chemically-active metal, such as iron (Fe). Resistance welding advantageously provides a secure attachment of the electrode material to the foil carrier without causing a deep fusion of the two materials being attached. The resulting shallow fusion contact, in turn, allows clean exposed electrode surface areas to be formed when the foil carrier is eventually chemically etched away, as explained below. Other types of attachment that result in shallow fusion of the electrode material and the foil carrier sheet material may also be used in lieu of resistance welding.

Attached to the metal carrier, the electrode contacts remain in a desired and stable position allowing easy connecting of the wiring system and subsequent molding of the polymer carrier. After completion of the molding process, the metal foil carrier is chemically etched away using a mixture of diluted acids, such as $HNO_3$ and HCl. The precious metal contacts and polymer are immune to the acid and remain in their intact, unaltered shape, and thereby provide the desired electrode array structure.

Figure 7A:
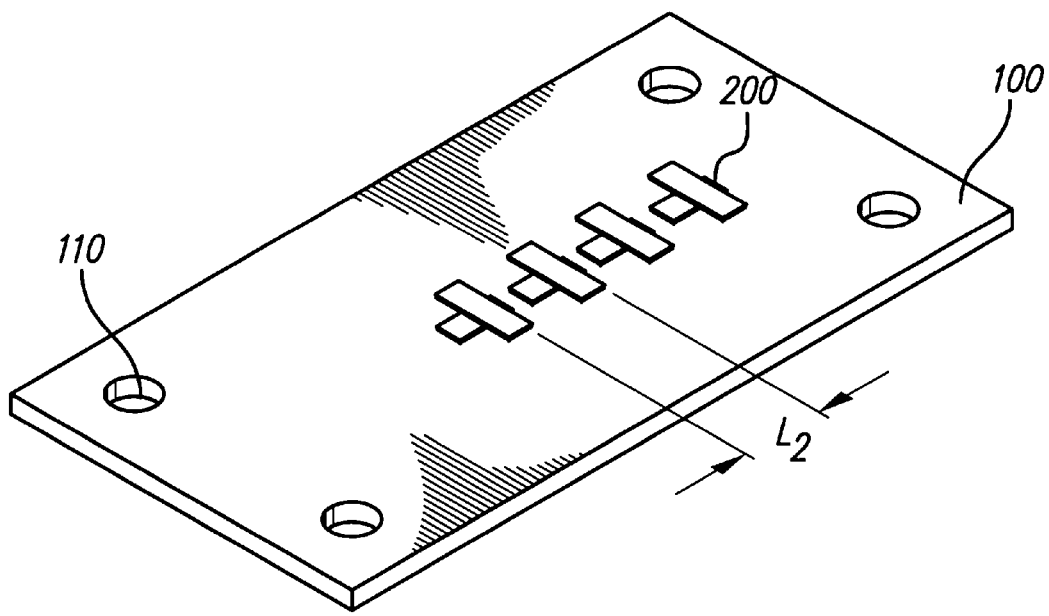
FIG. 7A depicts a preferred manner of making a multi-electrode contact array in accordance with the present invention.
Figure 7B:
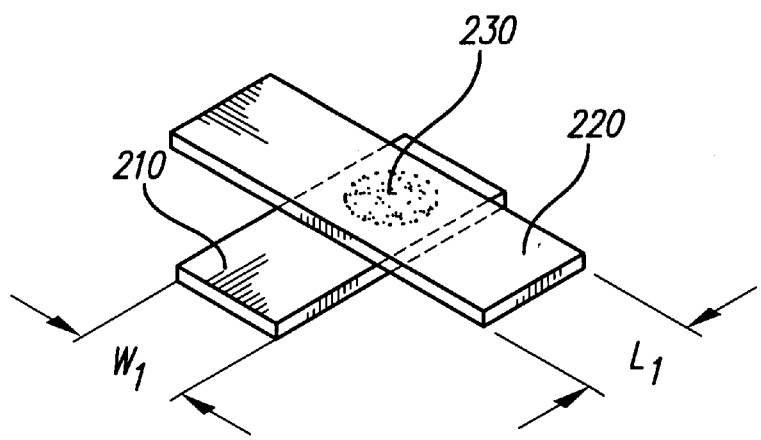
FIG. 7B shows an enlarged view the "T" strips used in making the electrode contacts of the array of FIG. 7A.

To illustrate the method, the method will be described relative to the fabrication of the electrode array 30 or 30' suitable for insertion into the cochlea. As a first step, an array of contacts 200 are resistance welded onto an iron carrier 100 so as to assume a desired in-line spaced-apart relationship, as shown in FIG. 7A. Each contact 200 consists of two pieces of platinum foil 210 and 220, connected together and joined to the carrier 100 by a shallow-fusion spot weld 230, as shown in FIG. 7B. The width of the strip 210 is approximately W1, and the width of the strip 220 is approximately L1. These strips are arranged to form a "T" shape, when viewed from a top view, with the strip 210 forming the leg of the "T", and with the strip 220 forming the cross bar of the "T". Moreover, the legs of each "T", are arranged in-line, with the proper spacing L2 therebetween, as shown in FIG. 7A.

As a second step, a wiring system is connected to each of the electrode contacts 200. This is accomplished as shown in FIGS. 8A, 8B, 8C and 8D. As seen in FIG. 8B, for example, an insulated wire 202', is laid on top of the electrode foil piece 220 (the cross bar of the "T"). The leg of the "T" of the foil piece 210 is then folded over to hold the end of the wire while the wire is welded in position (FIG. 8B). The welding process, preferably a resistance weld, burns away any insulation from the tip while making a secure mechanical and electrical connection between the wire and the electrode contact 200. The result is an electrode contact 200 having a wire 202' securely attached thereto (FIG. 8C). If other wires are present, e.g., going to more distal electrode contacts, then such wires may pass over the foil piece 210, lying more or less parallel to the wire 202' so as to form a bundle of wires 202. A similar bundle may be formed on the other side of the folded foil piece 210, thereby forming another wire bundle 203. The ends of the foil piece 220 are then folded upwards to form, in a preferred embodiment, a triangle, or Δ shape (as seen in a side view), as shown in FIG. 8D.

Figure 8A:
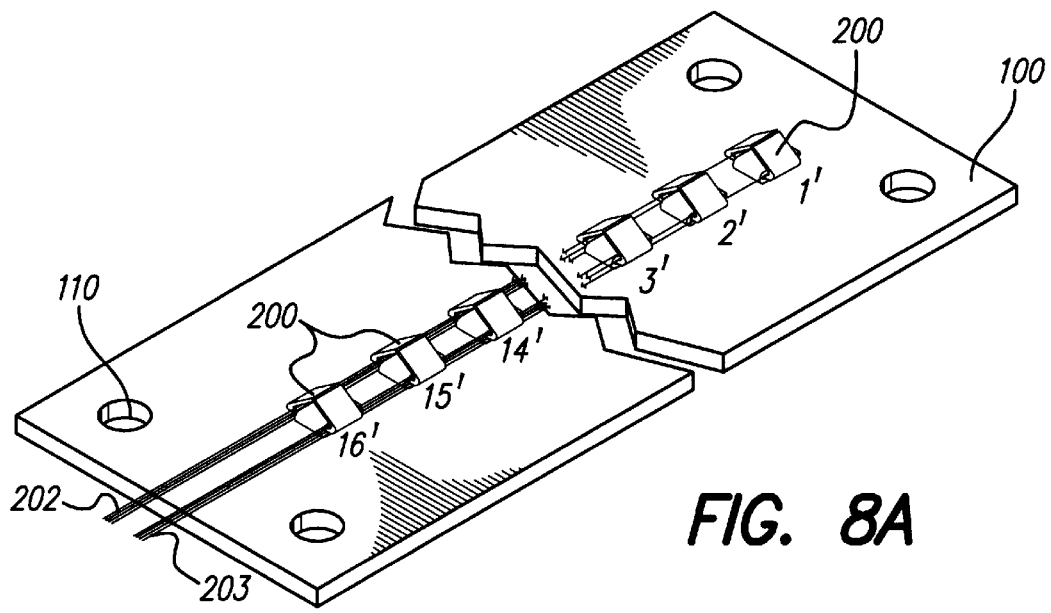
FIGS. 8A, 8B, 8C and 8D illustrate one manner in which wires are bonded and routed to each of the "T" strip electrode contacts of FIG. 7B during manufacture of the electrode array.
Figure 8B:
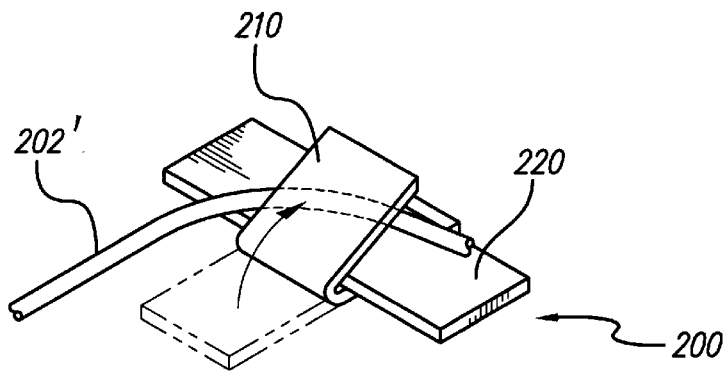
Figure 8C:
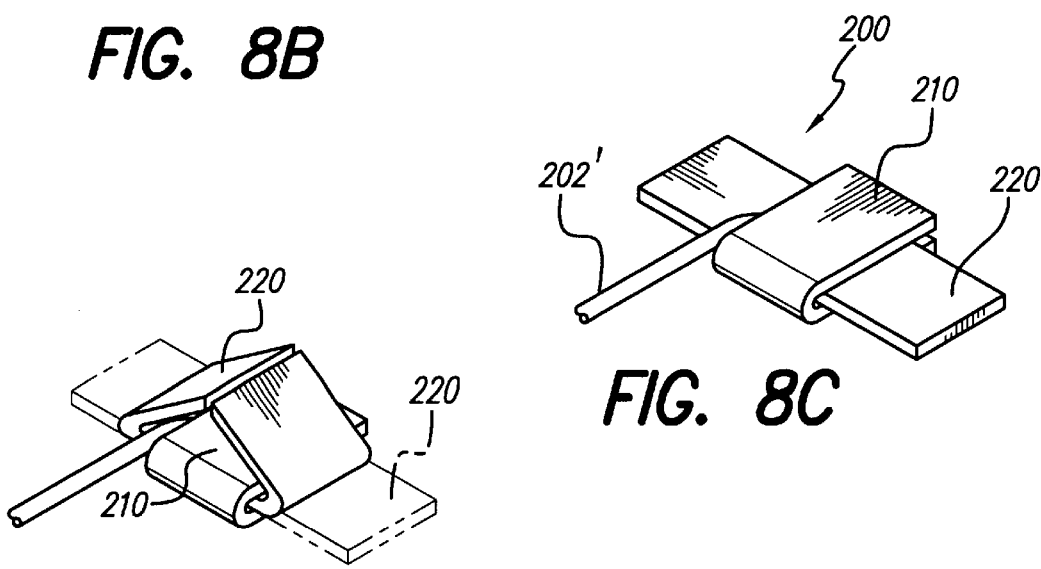
Figure 8D:
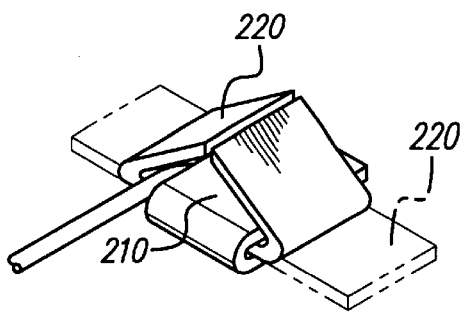

As seen in FIG. 8A, at least one wire from one of the bundles 202 or 203 is attached to the electrode contacts 2–16 in the manner described above. (For simplicity, only six of the sixteen or nineteen electrode contacts used in the electrode array 30 or 30' are shown in FIG. 8A,) Typically, a wire from wire bundle 202 will connect to electrode contact 16, and a wire from bundle 203 will connect to electrode contact 15, and so on, with adjacent in-line electrode contacts being connected to wires from alternating wire bundles. At least two wires, one from each bundle 202 and 203 remain for connection to the most distal electrode contact 1. In this fashion, at least seventeen wires are used to make electrical connection with sixteen electrode contacts. In the preferred embodiment, for example, the wire bundle 202 may contain 9 wires, and the wire bundle 203 may contain 8 wires, for the sixteen-electrode array 30 or 30' described herein. In general, the number of electrodes can be n and the number of wires can be at least n+1, where n is an integer of at least 8. The wire bundles 202 and 203 pass through the dummy electrode contacts, or reference marker contacts 34 (FIG. 1, 6), without making electrical contact therewith. For simplicity, the reference marker contacts 34 are not shown in FIG. 8A.

Having a wire bundle on each lateral side of each electrode contact, e.g., as seen in the sectional view of FIG. 5A or 6B, and hence on each lateral side of the electrode array, helps add lateral stability to the array. This is true even when the wire "bundle" only contains one wire. Thus, an important feature associated with using two wire bundles in the manner described is that the wire bundles help add stiffness to the electrode array in the lateral direction, but do not materially affect the ability of the array to flex or bend in the medial direction.

Figure 9:
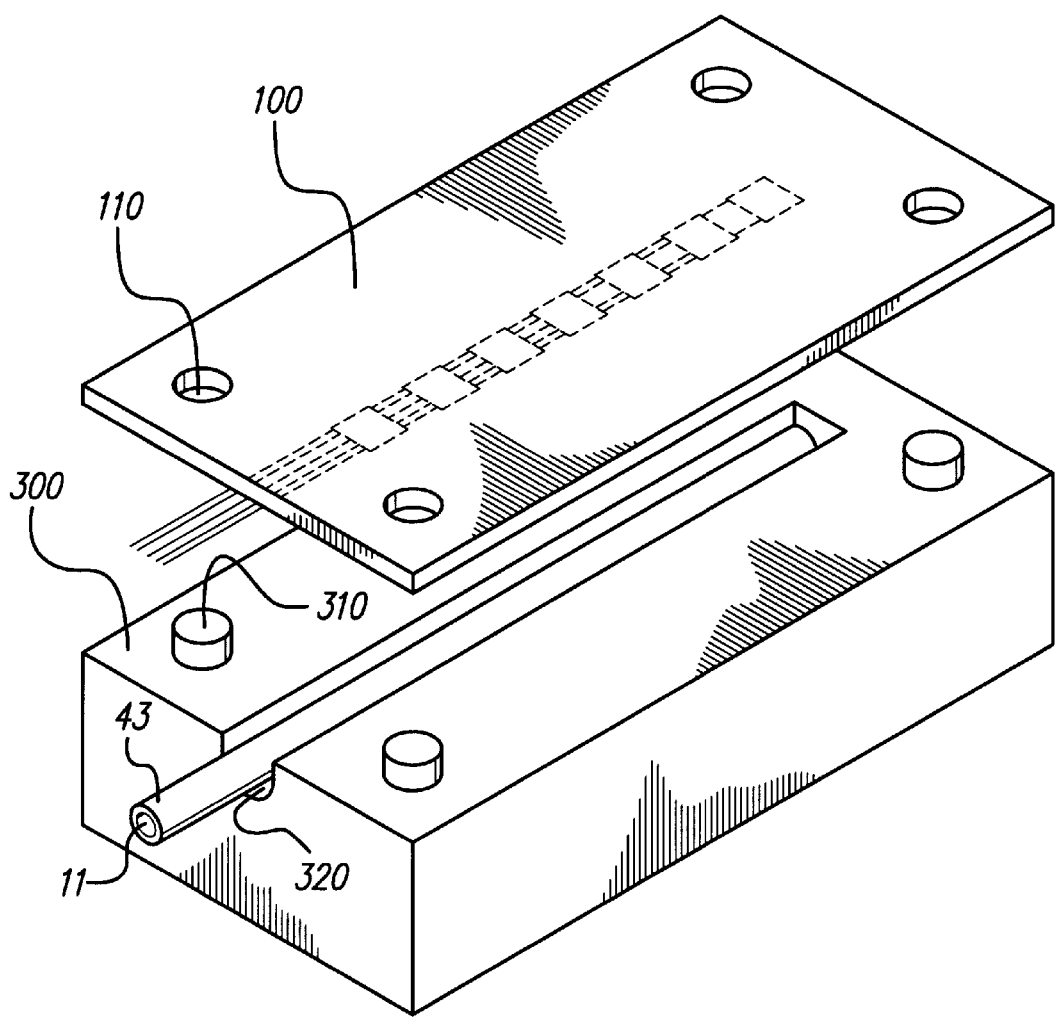
FIG. 9 depicts a molding die onto which the partially-formed electrode array of FIG. 7A, with wires attached to each of the electrodes as shown in FIGS. 8A–8D, may be mounted in order to form a straight polymer carrier for the electrode array.
Figure 10:
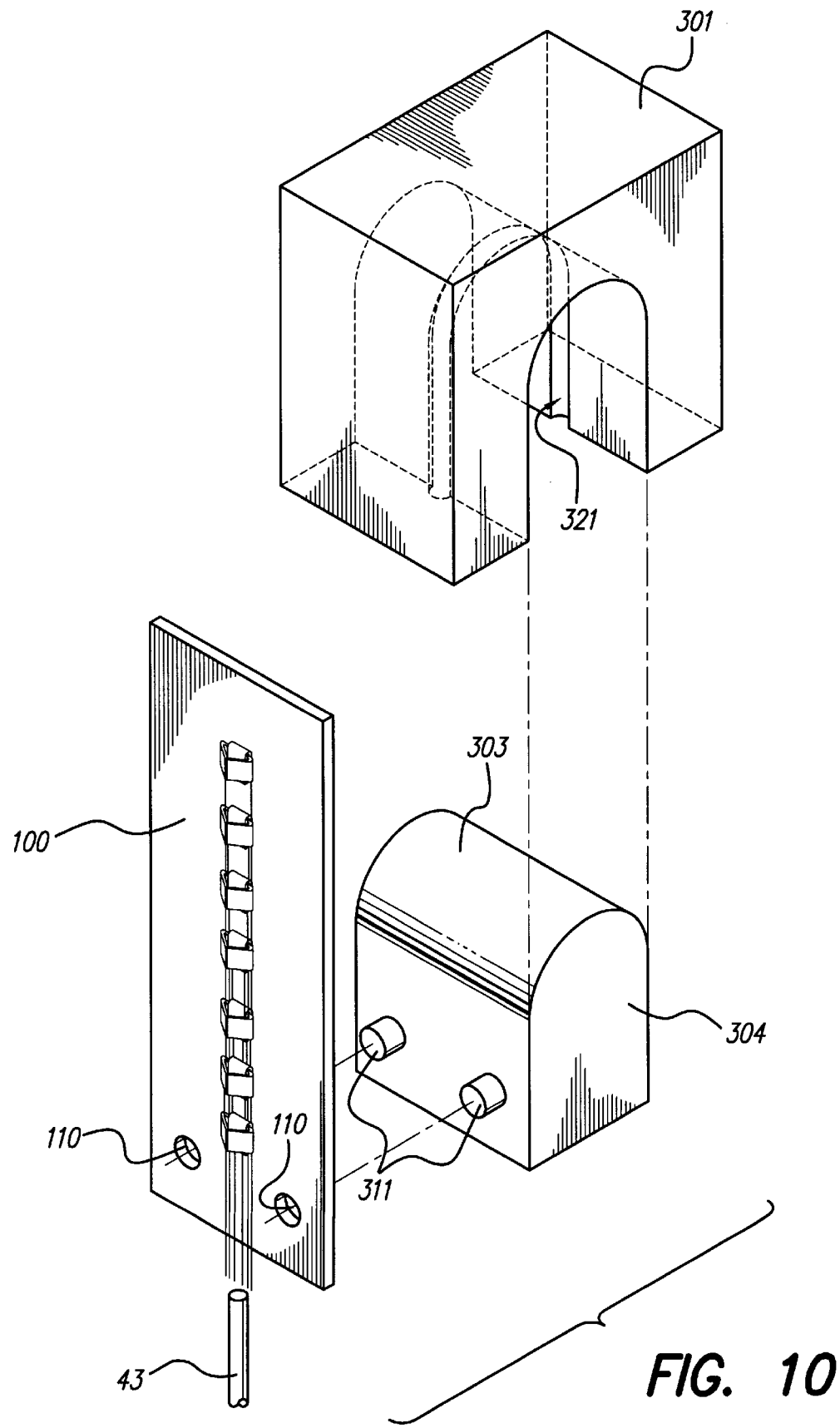
FIGS. 10 and 11 illustrate a perspective and side exploded view, respectively, of an alternative type of molding die onto which the partially-formed electrode array of FIG. 7A, with wires attached to each of the electrodes as shown in FIGS. 8A–8D, may be mounted in order to form a curved polymer carrier for the electrode array.
Figure 11:
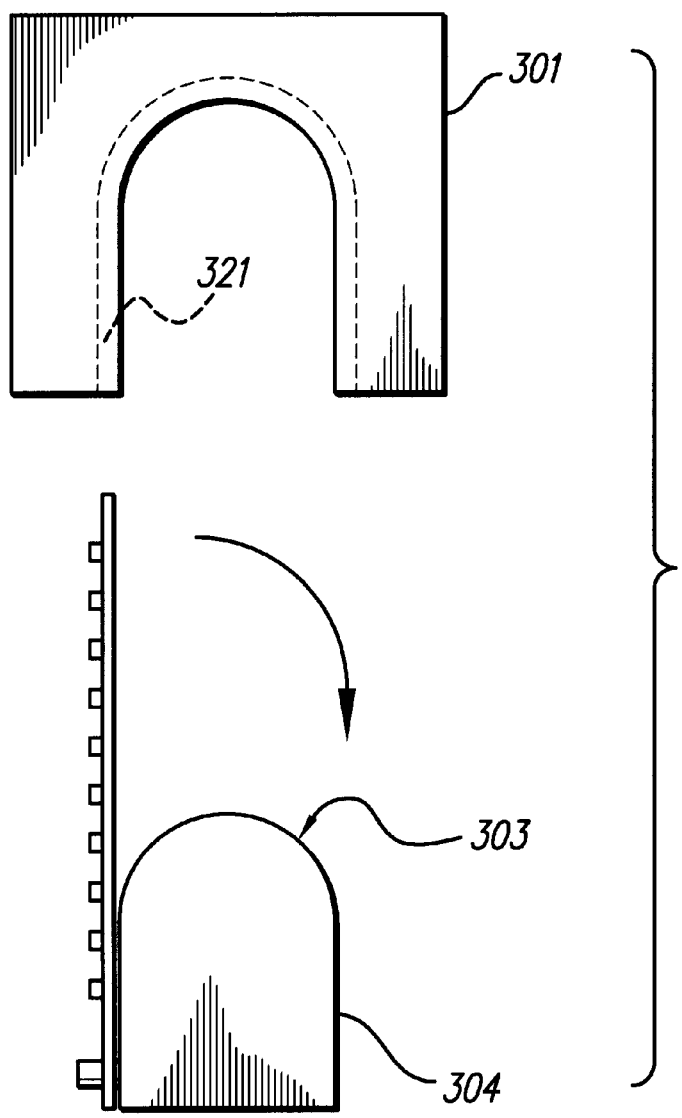

Once the wire bundles 202 and 203 have been connected to all of the active electrodes 200, the foil carrier 100 may be placed on a molding die 300 as shown in FIG. 9. The die 300 has alignment pegs 310 adapted to align with corresponding alignment holes 110 in the foil carrier 100. The die 300 further has a cavity or channel 320 formed therein into which the silicone tube 43, with channel 11 therethrough, may be positioned and the required amount of material, e.g., LSR-70, needed to form the polymer carrier 36 (FIGS. 4, 6) is injected around the tube 43. The LSR-70is then cured in conventional manner. This cavity or channel 320 may be shaped or formed as desired. The mold depicted in FIG. 9 would form a straight carrier 36 As an alternative to the flat-surface die 300 shown in FIG. 9, a curved die 301 is preferably used as shown in FIGS. 10 and 11. Such die 301 includes a curved surface 303 on a holding block 304 on which the foil carrier 100 may be placed. The block 304 has alignment pegs 311 adapted to align with corresponding alignment holes 110 in the foil carrier 100. The foil carrier 100 is placed on the block 304 and bent over the curved surface 303. The die 301 is then placed over the block 304, with the foil carrier 100 sandwiched therebetween. A channel or cavity 321 is formed in the die 301 having the desired shape and characteristics of the carrier that is to be formed through the molding process. The tube 43, with channel 11 therethrough, not shown in FIG. 11, over which the carrier 36 is molded, is positioned within the channel or cavity 321. The required amount of material to form the polymer carrier 36, e.g., LSR-70, is then injected into the channel and allowed to cure. By placing the foil carrier assembly 100 in the curved die of FIGS. 10 and 11 (note that FIG. 10 comprises a perspective view of the die 301 and block 304, and FIG. 11 comprises a side or profile view of the die 301 and block 304), the array can be molded or formed to assume a curved shape. Such curved shape may be preferred in some instances.

Thus, it is seen that through proper use of the die 300 or 301/304, or other dies, the electrode array may be formed to assume a natural curved shape, a slightly curved shape, or to be straight.

After the material used to form the carrier (e.g., LSR-70) cures, the foil carrier with the electrode array assembly (which is now molded inside of the polymer) is removed from the channel of the die 300 or 301/304 and placed in a mixture of diluted acids. The mixture of diluted acids dissolves the foil carrier 100, thereby exposing a clean surface of the electrode contacts 200. After washing to remove any residue of acids and Fe salts, the main electrode array structure is completed.

Advantageously, the structure of the electrode array 30, as seen best in the sectional view of FIG. 5A, or the electrode array 30', as seen best in the sectional view of FIG. 6B, bends or flexes more easily in the medial direction than in the lateral direction. That is, the electrode array, with its slight curved shaped, when inserted into the cochlea, is able to bend, as required, to follow the scala tympani duct of the cochlea (whether the right or left cochlea) as it is inserted deeper and deeper into such duct. As it does so, the electrode contacts 32 remain closest to and facing the modiolus wall, as desired. As the electrode array is inserted deeper into the cochlea, the electrode array does not easily twist, or bend laterally, which twisting or bending could move the electrode contacts away from the modiolus wall. This is because the electrode array is inherently stiffer in the lateral direction than in the medial direction due primarily to the presence of the wire bundles and folded/bent electrode contacts which provide an added degree of stiffness in the lateral direction.

To further understand one mechanism by which the present invention achieves flexing or bending in the medial direction, but resists such bending in a lateral direction (where the "medial" direction may be defined as the direction in which the electrode contacts face, and the "lateral" direction" may be defined as a direction perpendicular to both the medial direction and a longitudinal axis of the array), consider the following simplified model of the electrode array: The electrode contacts 32 may be viewed as rigid rectangular plates, hinged together by the flexible carrier material between each plate. Thus, sixteen such plates are hinged together in a long chain, each plate in the chain being connected to an adjacent plate in the chain by way of a hinged connection. Such chain of "hinged plates" may readily pivot about their respective hinged connections, thus easily and readily allowing the chain of hinged plates to bend in the medial direction. However, due to the rigid nature of each plate, bending in the lateral direction, assuming a perfect hinged connection, is virtually impossible. Even assuming a less-than-perfect hinged connection, bending in the lateral direction is still made difficult. This is because fixed-length wire bundles are embedded in the carrier on opposite lateral sides of the array. These "matched" (of equal length) wire bundles tend to make lateral bending or flexing more difficult because such lateral flexing or bending would typically require that one of the wire bundles increase in length, as the other decreases in length, as a lateral bend is made.

Because the electrode contacts of the electrode array disclosed herein remain facing and closest to the modiolus wall, stimulation of the cells embedded within the modiolus wall may occur at lower energy settings than would be required if the electrode contacts were not facing and closest to the modiolus wall. Hence, use of the present electrode array allows desired stimulation to be achieved at lower power levels. Lower power levels, in turn, mean that the overall cochlear stimulation system may operate on less power, which usually means a longer interval between battery replacement.

As described above, it is thus seen that the present invention provides an electrode array that is easy to manufacture and which provides enhanced performance when used. Such electrode array provides an array of spaced-apart electrodes along the medial side of the array. Upon insertion into the cochlea, a positioning stylet is inserted into a channel of the array, which stylet assumes a curved spiraling shape upon warming to body temperature, and causes the electrode contacts to face and hug the modiolus wall. The composition and makeup of the electrode array makes it easier to bend in the medial direction than in a sideways or lateral direction. Thus, the electrode contacts remain on the medial side of the electrode, hugging the modiolus wall, after the electrode is inserted into the cochlea.

While the invention herein disclosed has been described by means of specific embodiments and applications thereof, numerous modifications and variations could be made thereto by those skilled in the art without departing from the scope of the invention set forth in the claims.

What is claimed is:

1. An implantable electrode array insertable into a curved cavity for use with a tissue stimulation device the array comprising:

a flexible carrier having a proximal end, a distal end, a medial side, and a longitudinal channel passing from the proximal end to the distal end, the longitudinal channel being closed at the distal end;

at least eight electrodes having an exposed surface area on the medial side of the flexible carrier, the electrodes having an embedded portion behind the exposed surface area that extends into the flexible carrier;

a multiplicity of wires embedded within the flexible carrier, at least one wire of the multiplicity of wires being electrically and physically connected to a respective electrode;

wherein each electrode comprises first and second metallic strips formed in a "IT" shape, wherein a leg of the "T" is folded back over itself and holds at least one of the multiplicity of wires therebetween, the wire being electrically bonded to the folded T leg, and wherein sides of the "T" are folded upwardly into the flexible carrier; and a positioning stylet insertable into the channel of the flexible carrier, the positioning stylet comprising a memory wire having properties selected to coil the wire in a spiral shape when warmed to a temperature near 37° C.;

wherein when the electrode array is insertable in the curved cavity, with the medial side of the flexible carrier facing an inner wall of the curved cavity, and the positioning stylet is inserted into the channel and warmed to a temperature near 37° C., the flexible carrier assumes the spiral shape of the wire and is adopted to position the medial side of the flexible carrier against the inner wall, whereby the exposed surface area of the at least eight electrodes is adopted to be positioned adjacent the inner wall of the curved cavity.

2. The implantable electrode array of claim 1 wherein the positioning stylet comprises a memory wire having properties selected to form the spiral shape, the spiral shape matching an average curvature of a cochlear modiolus when warmed to a temperature near 37° C., and wherein the curved cavity into which the electrode array is insertable comprises a cochlea having a modiolar wall as the inner wall, whereby the at least eight electrodes are adopted to hug the modiolar wall when the positioning stylet is warmed to a temperature near 37° C.

3. The implantable electrode array of claim 2 wherein the memory wire is permanently held in the channel of the flexible carrier.

4. The implantable electrode array of claim 1 wherein a most distal electrode of the at least eight electrodes comprises a first electrode, and wherein a most proximal electrode comprises an nth electrode, where n is an integer of at least 8, and wherein the multiplicity of wires comprises at least n+1 wires, at least one wire being connected to each of the second through nth electrodes, and at least two wires being connected to the first electrode.

5. The implantable electrode array of claim 4 wherein the at least n+1 wires are separated into two bundles, a first bundle being routed along one lateral side of the electrode array and a second bundle being routed along the other lateral side of the electrode array, wherein both wire bundles are engaged by the electrodes they pass by, and wherein both wire bundles are embedded within the flexible carrier, and wherein at least one wire connected to the first electrode comes from the first bundle, and wherein at least one other wire connected to the first electrode comes from the second wire bundle.

6. The implantable electrode array of claim 1 further including a hump formed on the medial side of the array in the space between the exposed surface area of each electrode.

7. The implantable electrode array of claim 1 wherein the electrode array comprises an implantable cochlear electrode array adapted for insertion into a cochlea of a patient, and wherein each electrode has an exposed contact surface area no smaller than approximately 0.16 mm$^2$.

8. An implantable cochlear electrode array insertable into a human cochlea, the cochlea spiraling around a cochlear modiolus, the cochlear electrode array comprising:

an elongate flexible carrier having a proximal end, a distal end, a medial side, a longitudinal axis, and a longitudinal channel passing through the flexible carrier in substantial alignment with the longitudinal axis, the channel being open at the proximal end of the flexible carrier and closed at the distal end of the flexible carrier;

at least n spaced-apart electrodes embedded within the flexible carrier, each electrode having a surface area exposed on the medial side of the flexible carrier, where n is an integer of at least 8, and wherein a most distal electrode comprises a first electrode, and wherein a most proximal electrode comprises an nth electrode;

at least n+1 wires embedded within the flexible carrier, at least one wire being connected to each of the second through nth electrodes, and at least two wires being connected to the first electrode; and a positioning memory wire insertable into the channel, the positioning memory wire having properties selected to produce a transformation to a spiral shape at temperatures near body temperature, and allowing the memory wire to be straightened at temperatures substantially less than body temperature;

wherein the spiral shape of the memory wire at temperatures near body temperature comprises a shape resembling the average curvature of the cochlear modiolus; and whereby when the array is insertable into the cochlea with the carrier medial side facing the modiolus, and when the memory wire is inserted into the channel, the electrode array is adapted to hug the modiolus, with the exposed surface area of the electrodes adapted to be positioned adjacent the modiolus.

9. The implantable cochlear electrode array as set forth in claim 8 further including a hump formed on the elongate flexible carrier on the medial side in the space between the exposed surface area of each electrode.

10. The implantable cochlear electrode array of claim 8 wherein the electrode array is more flexible in a medial direction than in a lateral direction, where the medial direction comprises a direction perpendicular to the medial side, and where the lateral direction comprises a direction perpendicular to the medial direction and the longitudinal axis.

11. The implantable cochlear electrode array as set forth in claim 10 wherein the elongate flexible carrier has a natural curve in the medial direction.

12. An implantable cochlear electrode array insertable into a human cochlea, the cochlea spiraling around a cochlear modiolus, the cochlear electrode array comprising:

an elongate flexible carrier having a proximal end, a distal end, a medial side, and positioning means carried by the flexible carrier for transforming the flexible carrier to a spiral shape at temperatures near body temperature, the spiral shape comprising a shape resembling the average curvature of the cochlear modiolus;

at least eight spaced-apart electrodes embedded within the flexible carrier, each electrode having a surface area exposed on the medial side of the flexible carrier;

at least nine wires embedded within the flexible carrier, at least two wires being connected to a most distal electrode, and at least one wire being connected to each of the remaining electrodes; and wherein when the array is insertable into the cochlea with the medial side facing the modiolus, the electrode array warms to body temperature, transforms to the spiral shape, and is adopted to hug the modiolus, with the exposed surface area of the electrodes adopted to be positioned adjacent the modiolus.

13. The implantable cochlear electrode array of claim 12 wherein the positioning means carried by the flexible carrier comprises a positioning memory wire carried within the flexible carrier, the positioning memory wire having properties selected to produce a transformation to the spiral shape at temperatures near body temperature, and allowing the memory wire to be straightened at temperatures substantially less than body temperature.

14. The implantable cochlear electrode array of claim 12 wherein the flexible carrier has a channel passing longitudinally therethrough, and wherein the positioning means comprises a positioning memory wire removably insertable within the channel of the flexible carrier, the positioning memory wire having properties selected to produce a transformation to the spiral shape at temperatures near body temperature, and allowing the memory wire to be straightened at temperatures substantially less than body temperature.

* * * * *